United States Patent [19]
White et al.

[11] Patent Number: 5,242,425
[45] Date of Patent: Sep. 7, 1993

[54] ANTISEPTIC CATHETER COUPLING SEPTUM

[75] Inventors: George W. White, El Toro; Jack W. Brown, Santa Ana; Lisa A. Tam, Long Beach, all of Calif.

[73] Assignee: Gish Biomedical, Inc., Irvine, Calif.

[21] Appl. No.: 791,362

[22] Filed: Nov. 14, 1991

[51] Int. Cl.⁵ .......................................... A61M 25/00
[52] U.S. Cl. ................................. 604/256; 604/265; 604/283; 604/905
[58] Field of Search .............. 604/29, 167, 175, 199, 604/201, 86–88, 244, 256, 265, 283, 905

[56] References Cited

U.S. PATENT DOCUMENTS

| | | | |
|---|---|---|---|
| 3,502,097 | 3/1970 | Muller | 604/283 |
| 4,346,703 | 8/1982 | Dennehey et al. | 604/905 |
| 4,417,890 | 11/1983 | Dennehey et al. | 604/905 |
| 4,440,207 | 4/1984 | Genatempo et al. | 604/905 |
| 4,559,043 | 12/1985 | Whitehouse et al. | 604/243 |
| 4,610,469 | 9/1986 | Wolff-Mooij | 604/905 |
| 4,752,292 | 6/1988 | Lopez et al. | 604/283 |
| 4,781,693 | 11/1983 | Martinez et al. | 604/244 |
| 4,919,658 | 4/1990 | Badia | 604/265 |
| 5,139,483 | 8/1992 | Ryan | 604/86 |

Primary Examiner—John D. Yasko
Assistant Examiner—Anthony Gutkowski
Attorney, Agent, or Firm—George F. Bethel; Patience K. Bethel

[57] ABSTRACT

A plastic coupler for a catheter assembly including a distal member for attachment to a catheter tube and having a female luer lock connector for separable interconnection with a male connector of a proximal member having a self-sealing material disposed within a through passage for injection and a outer protective cap containing a sponge saturated with an antiseptic to bathe the self-sealing material and interconnection with an antiseptic, and a method for maintaining a coupler for a catheter assembly in aseptic condition.

12 Claims, 3 Drawing Sheets

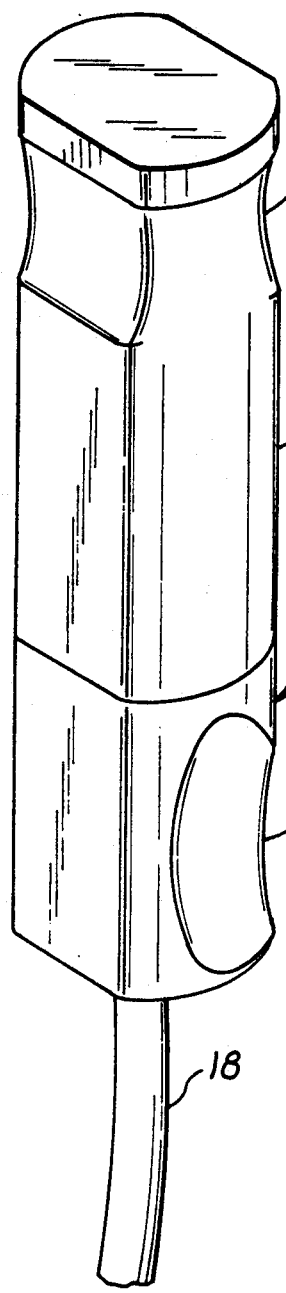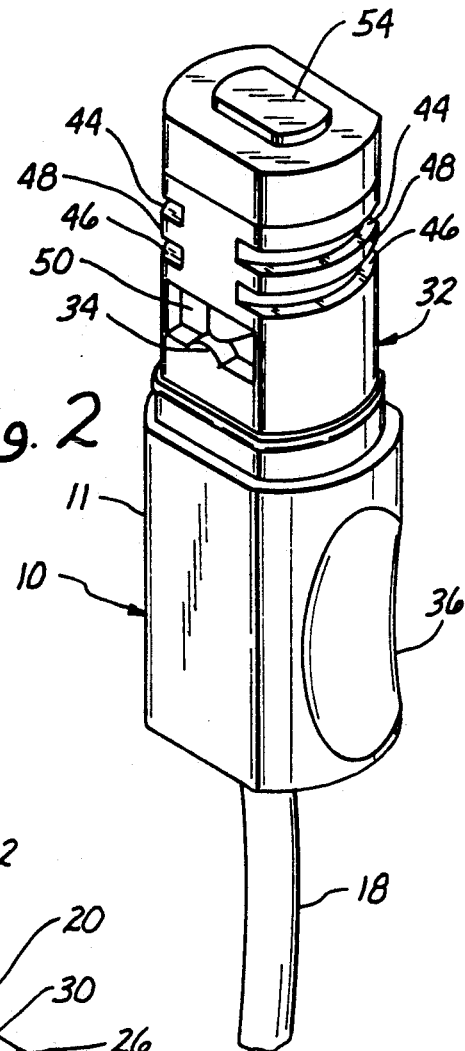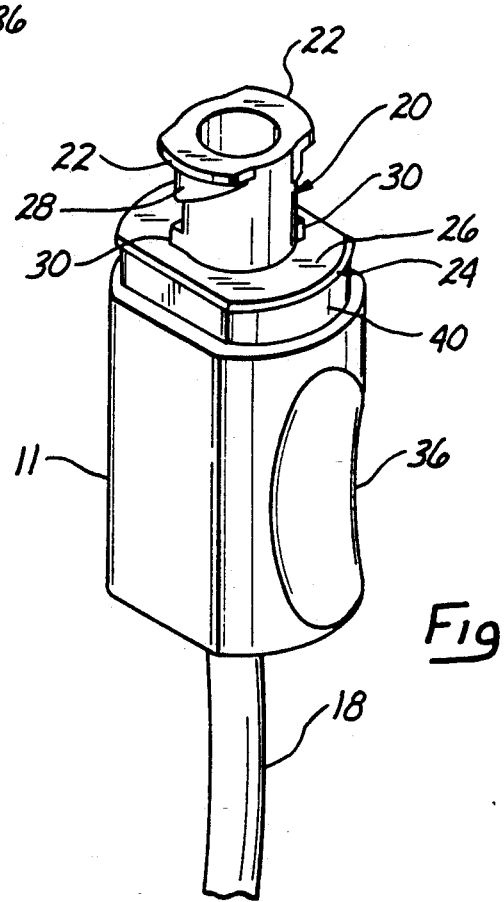

ANTISEPTIC CATHETER COUPLING SEPTUM

FIELD OF THE INVENTION

The field of the invention lies within the medical art. More particularly, the field lies within the art of medical catheters including indwelling catheters for the introduction of various medical fluids including, for example, chemotherapeutic agents, nutritional liquids, and drug delivery to a patient.

BACKGROUND OF THE INVENTION

Description of the Prior Art

The medical catheters of the prior art include among others an extremely flexible soft catheter attached to a coupler including a generally rigid housing suitable for grasping between the thumb and forefinger. The coupler housing has an exterior rigid tube or bushing for insertion within the lumen of a soft flexible catheter tubing leading to a patient. Flow through the flexible tubing is controlled by a finger operated clamp.

The coupler housing also includes an exterior female luer connector having a central passage which is in communication with the rigid tube and flexible tubing. An outer peripheral lipped area on the female luer connector is designed for interlocking with a male luer connector of a protective cap or with a male luer connector on a syringe or other device. The male luer connector includes a tubular member which is axially disposed within an interiorly threaded member for seating tightly within a female luer connector for communication with the central passage of the coupler. Alternately, the female luer connector is exteriorly threaded.

The female luer connector on the coupler is interlocked with the male luer connector on the syringe or other device by insertion, followed by a twist action. Separation of the female luer connector of the coupler from the male luer connector on the cap or syringe can be achieved by a reverse twist and then pulling apart. The locking assembly which has just been described is generally known in the art as a luer lock assembly.

This design has been extremely well received due to the ease with which a syringe or other male luer connectors containing needed medicines can be secured and later removed.

In recent years, however, it has been found that pathogens have been introduced into the catheter by means of injection, by touch, or perhaps by the spilling of a medicine or a nutritional fluid onto the female luer connector on the coupler. Also, occasionally the needle will damage or perforate the flexible tube during insertion risking the introduction of contaminated air or loss of fluids.

Generally, the female luer connector of the coupler and the male luer connector of the syringe are each provided with a protective cap prior to joining. That is, there is a cap over the female luer member of the coupler. Also, there is a cap over the male luer connector on the syringe. Prior to the joining of the two respective parts, the caps are removed. This reduces but does not eliminate the possibility of introducing pathogens into the body of a patient.

This has led to the addition of an injection cap containing a self-sealing material through which a needle is inserted. The material seals itself after removal of the needle. The injection cap is joined to the female luer connector and can be removed if desired for other direct connection to the female luer connector. It was found, however, that pathogens were still entering the catheter is spite of the provisions to prevent such occurrence. This was especially true with respect to the threaded areas within connecting parts.

In an effort to further minimize the possibility of introducing pathogens into a catheter, applicant has invented a new catheter assembly having several provisions for avoiding the introduction of pathogens and also for avoiding damage to the flexible catheter tubing.

As a consequence, it is an object of the invention to provide a capped catheter assembly having a coupler formed in two major separable pieces, one of which includes a self-sealing septum.

It is a further object of the invention to provide a means for preserving the self-sealing septum and the connection between the major pieces in an aseptic condition.

It is another object of the invention to provide a catheter assembly having a coupler embodying a standard female luer lock fitting with a removable interlocking male luer connection having a self-sealing septum.

It is an object of the invention to provide a catheter assembly having an interlocking two part coupler which permits the removal and replacement of an outer connecting part of the coupler.

It is another object of the invention to provide a catheter assembly having a coupler of two separable interconnecting major parts including a self-sealing septum. An outer protective cap has an antiseptic means disposed within the protective cap so that when the coupler is capped the antiseptic means is in contact with the self-sealing septum and with the interconnection between the major parts of the coupler.

It is a final object of the invention to provide a catheter assembly having a coupler of two separable, interconnecting major parts including an injection cap having a self-sealing septum and an outer protective cap containing antiseptic means which at the same time provides a low profile shape having a smooth exterior surface which will not catch on clothing or cause discomfort to the patient. The unique flattened configuration avoids twisting and facilitates taping.

As used herein and in the appended claims with respect to the catheter assembly, the term "distal" refers to the forward end of the catheter which is inserted into the patient's body. The term "proximal" refers to the trailing, exposed end of the catheter assembly which is external to the patient's body.

SUMMARY OF THE INVENTION

A catheter assembly is provided including a coupler having a distal member and a proximal interconnecting member having a self-sealing septum. An outer protective cap extends over the proximal interconnecting member to cover the self-sealing septum and the connection between the distal member and the proximal member. The outer protective cap contains an antiseptic for purposes of contacting the self-sealing septum and the interconnection to provide an aseptic condition. According to a preferred embodiment an absorbent material is saturated with the antiseptic and inserted within the outer protective cap.

The coupler is formed mainly in two separable, connecting parts. The distal member or part contains a hard tube or bushing for insertion within the lumen of a flexible catheter tube. A hard boot or sleeve, coextensive with the bushing, encloses the bushing and inserted catheter tube. The boot is suitable for grasping between thumb and forefinger.

The distal member is also provided with a hub and an outer female luer connector opposite the bushing and catheter tubing connection. The outer female luer connector preferably contains two small, opposed flanges or ears on its outer edge surrounding a central passage which is in communication with the hard tube and flexible catheter tubing. Alternately, the outer female luer connector is exteriorly threaded.

The second or proximal interconnecting part or injection cap of the coupler preferably has a generally flattened tubular shape. It is preferably formed at one end with opposed apertures or openings for receipt and retention of the two small, opposed flanges on the distal member.

As an alternate embodiment, the proximal member or injection cap can be formed with a circular cross section.

One end of the proximal member is provided with spaced grooves and a land for ease in grasping. The interior of the proximal member is provided with a central, preferably tapered passage which upon insertion within the distal member provides communication with the flexible catheter tubing.

At the outer end of the central passage of the proximal member is a collar for receipt of a flexible self-sealing septum. The septum is held in place by an end cap having a central opening which slip-fits over the collar leaving the central area free and exposing a portion of the septum surface for injection with a needle.

The proximal member or injection cap is entirely covered by an outer protective cap. The outer protective cap is preferably friction fit but can be internally threaded for threaded connection to the distal member. The outer protective cap preferably contains a sponge at its base which is saturated with an antiseptic such as povidone-iodine solution or the like. When capped, the antiseptic contacts the outer exposed surface of the self-sealing septum and flows into contact with the septum and flows along the walls of the proximal member and into contact with the interconnection between the distal and proximal members to keep the septum and interconnection in aseptic condition.

This arrangement permits the removal of the outer protective cap without touching the septum. A syringe containing a needle can be inserted within the septum for delivery of medicine or other liquid. Upon removal of the needle from the septum, the septum seals itself against entry of pathogens. Preferably a fresh, new outer protective cap is then placed on the coupler which places a fresh antiseptic solution into contact with the outer surface of the septum and with the interconnection. This effectively allows the surface of the septum and interconnection to be pathogen free for the next injection.

Occasionally, it is desirable to connect an I.V. to the catheter assembly. In this instance, the outer protective cap is removed followed by removal of the proximal member or injection cap. This exposes the female luer connector for direct interconnection with a male luer connector of an I.V. or the like. Since the antiseptic material has been in contact with the interconnection, the introduction of pathogens into the catheter is minimized.

Each time the outer protective cap is removed for any reason, it is preferably replaced with a new outer protective cap containing a fresh antiseptic solution. This procedure insures full contact of fresh antiseptic with the septum and with the interconnection between the proximal and distal members.

When the proximal member becomes worn or otherwise degraded, it can be replaced along with the outer protective cap to preserve aseptic conditions and to avoid the need for replacement of the catheter tube and distal member.

BRIEF DESCRIPTION OF THE DRAWINGS

The invention will be more readily understood by reference to the attached drawings in which:

FIG. 1 shows a perspective view of the capped catheter assembly of the invention.

FIG. 2 shows a perspective view of the capped catheter assembly of FIG. 1 with the outer protective cap removed.

FIG. 3 shows a perspective view of the catheter assembly of the invention with the proximal member containing the self-sealing septum removed.

DETAILED DESCRIPTION OF THE INVENTION

Figure 4:
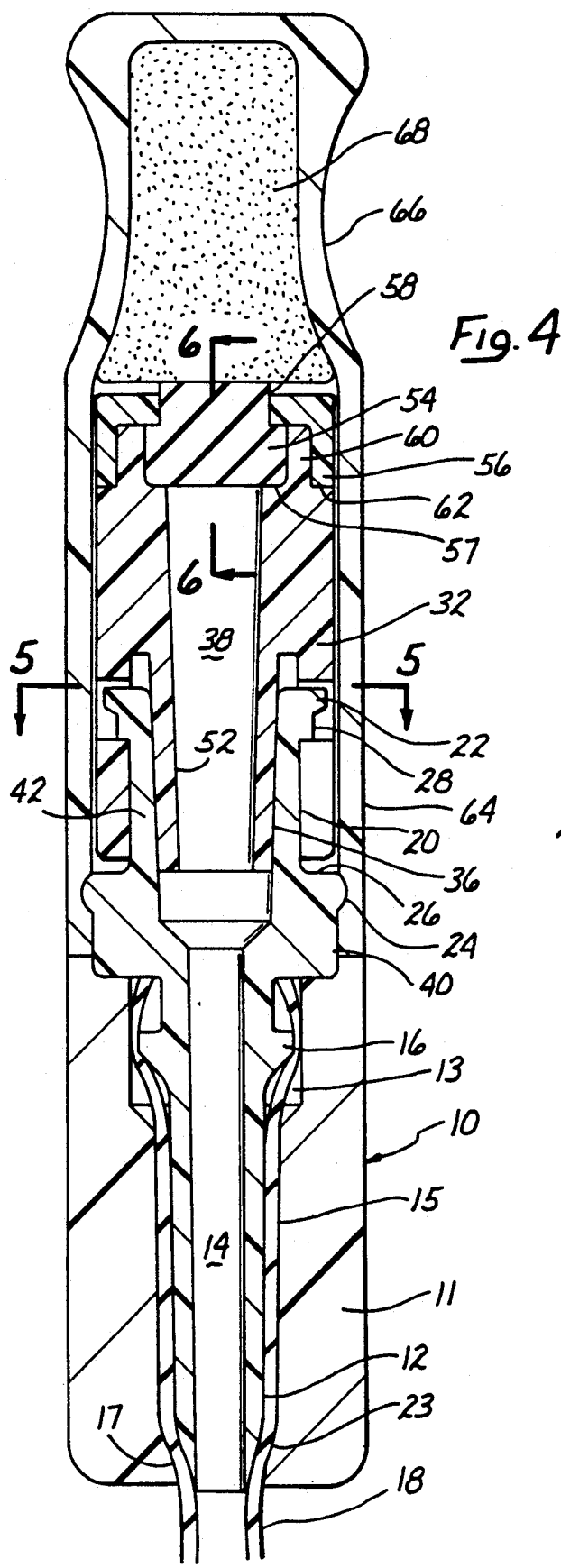
FIG. 4 shows a lengthwise section of the catheter assembly of the invention.

Referring to FIG. 4, there is shown a lengthwise section of the catheter assembly of the invention. It can be seen that the catheter assembly includes a flexible catheter tube 18 which is secured to a coupler which is formed in two separable main parts, a distal part 10 and a proximal part or injection cap 32. The coupler is covered by an outer protective cap 64.

Preferably, the coupler including the distal member 10 and the proximal member 32 is formed of a rigid plastic material suitable for medical use although other materials such as metals or glass can also be used.

Excellent results have been obtained using a transparent plastic such as polymethylpentene for the proximal member or injection cap 32. In addition to transparency, this plastic exhibits chemical stability, can be sonic welded and has a relatively soft durometer rating.

The distal member is preferably formed of an alloy of polycarbonate and copolyester. This plastic is preferably more rigid than the proximal member.

Other plastics for the distal or proximal member will be obvious to those skilled in the art. Any plastics used are preferably chemically stable and are preferably able to be joined by R F welding, vibration welding, solvent bonding and the like. Most preferably the plastic used for the proximal member has a softer durometer rating than the plastic used for the distal member. The exact plastic or other material used is not critical and should not limit the scope of the invention.

The first main part of distal member 10 has a hub 40 from while a male member or bushing 12 extends distally and a female luer member 20 extends proximally. The male member 12 is tapered at its end 23 and has an exterior ridge 16 spaced from hub 40. An internal central passage 14 extends through male member 12 and communicates with a central passage or bore within hub 40 and exterior projecting female luer member 20.

Male member 12 is inserted within the lumen of a flexible catheter tubing 18 from the tapered end 23 to and over the ridge 16. The catheter tubing 18 is held in place in part by means of ridge 16.

Base member or boot 11 has a central passage 15 which opens into an enlarged chamber 13 and is tapered at its open end 17. Male member or bushing 12 and catheter tubing 18 are spaced from and axially disposed within central passage 15 of boot 11 with its ridge 16 in enlarged chamber 13 and with its tapered end 23 disposed within tapered end 17 of passage 15 of member 11.

In order to secure the catheter tube 18 within distal member 10, base member or boot 11 is joined to hub 40. Preferably sonic welding is used but R F welding, vibration welding, solvent welding or equivalent method can also be used. The exact method used is not critical. The effect is to provide a continuous passage within flexible catheter tubing 18, central passage 14 of male member 12 and hub 40, and into a central passage 36 of projecting female luer member 20.

Projecting female luer member 20 extends proximally from hub 40. Hub 40 is in the form of an enlarged diameter member having a shoulder 26 with a peripheral ridge 24 surrounding the shoulder 26.

Figure 5:
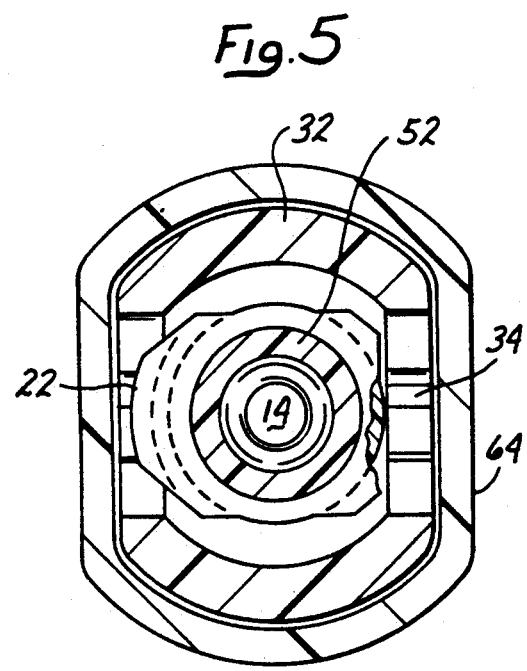
FIG. 5 shows a cross section taken along the lines 5—5 of FIG. 4.

Projecting female luer member 20 is preferably formed with an upwardly extending tubular projection 42 of lesser diameter than hub 40. Tubular projection 42 has an outer pair of diametrically opposed lips or ears 22. The lips 22 can also be seen in FIGS. 3 and 5.

As shown in FIG. 3, underlying each lip or ear 22 is a flange or ridge 28, each of which is slanted upwardly on one side towards the lip 22.

As can best be seen in FIG. 3, projecting female luer member 20 is provided with a pair of stops 30 adjacent hub 40. These stops 30 act to precisely stop female luer member 20 when connected to a secondary proximal member or connector 32 in the manner to be described and shown in FIG. 2.

FIG. 2 shows the distal member 10 and the proximal member 32 joined together. Another view can be seen in the section of FIG. 4.

As shown, proximal member or injection cap 32 has a generally oval cross section which is preferably flattened on two opposite sides and rounded or curved on two opposite sides. On the rounded sides near the top are a pair of grooves 44 and 46 and a land 48 disposed between them to facilitate grasping. On the lower portion on each of the flattened sides is an opening or aperture 50. Each aperture 50 has a raised tab 34 on its lower edge.

Axially disposed within the lower end of proximal connector 32 is tube 52 having an open central passage 38. Tube 52 extends slightly beyond the end of the lower portion of connector 32 for tight connection within female luer member 20. Surrounding the top of central passage 38 is a collar 60 which is spaced from a surrounding ledge 62.

Figure 6:
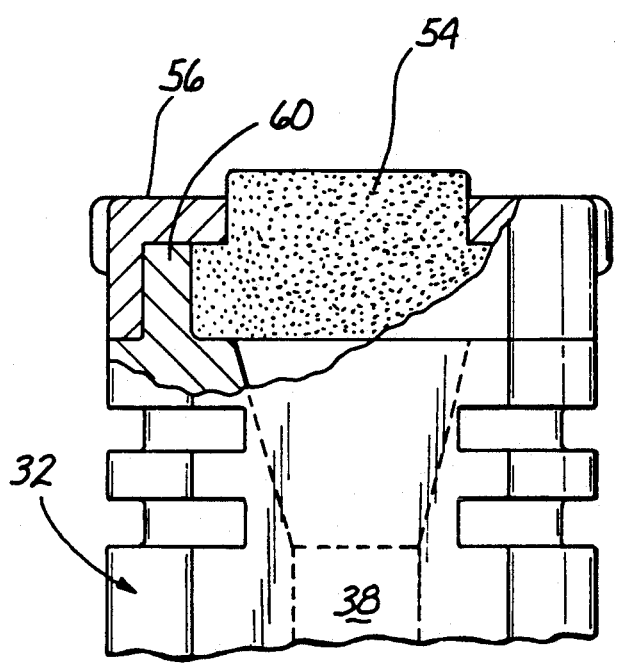
FIG. 6 shows a partial lengthwise section taken along the lines 6—6 of FIG. 4.

As shown in the cross section of FIG. 6, the upper portion of passage 38 preferably has a flattened oval configuration. As indicated also in FIGS. 2 and 4, a self-sealing septum of a silicone silastic, polyisoprene or other self-sealing natural or synthetic elastomeric material 54 is inserted within collar 60 and stopped by resting on an interior rim 57 within passage 38 at the base of collar 60. A retaining end cap 56 having a preferably flattened central opening 58 as shown in FIGS. 2 and 4 permits the septum 54 to protrude slightly through the opening 58 and facilitate injection with a needle. The oval cross section of the upper section of passage 38 together with its tapered configuration also facilitates injection with a needle.

It should be understood that the invention is not limited by the type of self-sealing material used and other equivalent materials will be obvious to those skilled in the art.

The end cap 56 is sized to be slip-fit over collar 60 of member 32. When in place, end cap 56 fits over collar 60 and rests on border rim or ledge 62 of member 32. The end cap 56 is preferably sonic welded to the rim 62 and collar 60. Other methods such as R F welding, vibration welding, solvent welding, or the like methods can alternately be used.

Proximal connection or injection cap 32 is preferably formed of a transparent plastic. The advantage is to enable visual verification of removal of all air bubbles in passage 38. Also, transparency enables the easy determination of contact of the antiseptic solution with the septum and with the interconnecting parts of the coupler.

As noted above, the proximal connector 32 interlocks with distal member 10 to provide a continuous passage within flexible catheter tubing 18, central passage 14 of male member 12 and hub 40, central passage 36 of projecting female luer member 20, and central passage 38 of connector 32. This continuous passage is shown in the interlocking condition in FIG. 4. Thus, entry into the continuous passage can be achieved only by penetration of self-sealing septum 54 as by a needle.

Distal member 10 and proximal member 32 are joined together by insertion of tube 52 of proximal member 32 into female luer member 20 of distal member 10. A slight twist of the two respective members 10 and 32 permits the lips 22 of female luer member 20 to enter aperture 50 of proximal member 32. At the same time, the flange 28 engages the tab 34 of aperture 50 on member 32.

A very tight fit is thereby achieved with proximal member 32 abutting stops 30. With this section, the lower portion of tube 52 is tightly inserted within central passage 36 of projecting female luer member 20 of member 10. A twist of approximately 90 degrees will very tightly engage female luer member 20 with proximal member 32 so that the two members are in a fluid tight relationship for low pressures. A reverse twist of the two members can readily disengage the two parts.

An outer protective cap 64 having finger grips 66 is preferably slip-fit over the assembled members 10 and 32. The outer protective cap 64 is preferably retained by peripheral ridge 24 of shoulder 26 of hub 40. Preferably, within the outer protective cap 64 is a sponge 68 saturated with a disinfectant or antiseptic material such as povidone-iodine solution. The invention is not limited by the type of antiseptic used. While an absorbent material is preferred, its use is not critical to the invention.

When the outer protective cap 64 is in place, the sponge 68 with antiseptic material is in contact with the exposed surface of self-sealing septum 54. At the same time the antiseptic material is forced within a space between proximal member 10 and outer protective cap 64. This permits the antiseptic to flow into apertures 50 of proximal member 32 so that the connection between female member 20 and proximal member 32 is bathed with antiseptic.

In operation, the assembly as shown in FIG. 4 protects the self-sealing septum from the introduction of bacteria or other pathogens. Removal of the outer protective cap 64 reveals the surface of the self-sealing septum 54. A needle can then be inserted through the self-sealing septum 54 for injection of medicine or other fluids into the passage 38 for introduction into catheter tubing 18. Withdrawal of a needle form the self-sealing septum 54 permits the surface to seal itself against the introduction of bacteria, other pathogens, or air. Preferably, a new outer protective cap 66 containing fresh antiseptic is then placed on the coupler and the old outer protective cap discarded.

If desired, the proximal connector 32 can be removed for direct connection between female luer member 20 of distal member 10 and a device equipped with a male luer interlocking feature. The antiseptic which has been held in contact with the connection between female member 20 and proximal member 32 preserves these parts in aseptic condition.

A particular advantage of the invention is the provision of a catheter assembly unit having its interconnecting luer parts and a self-sealing septum maintained in aseptic condition.

Figure 7:
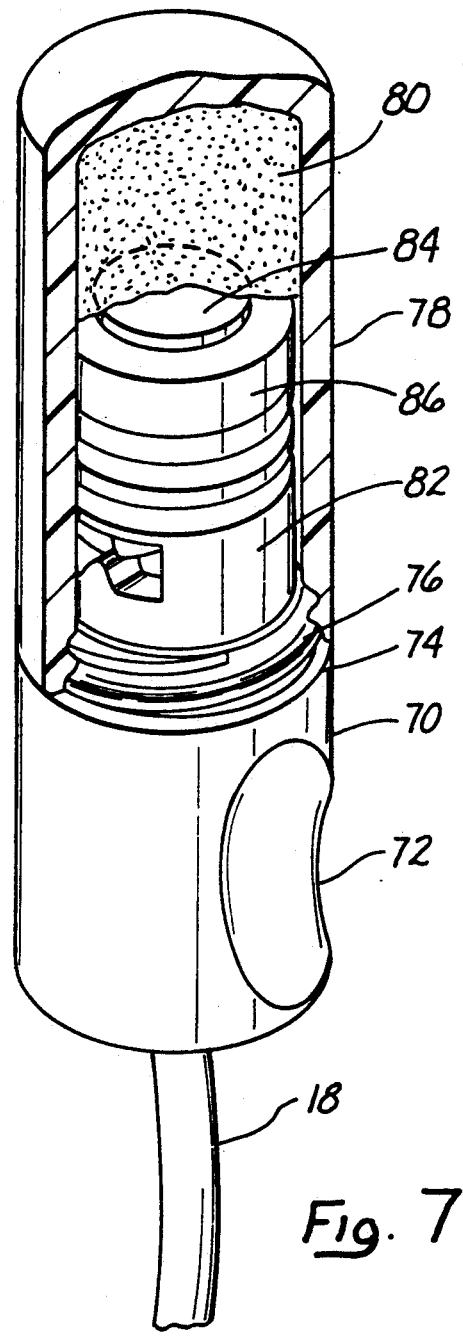
FIG. 7 shows an alternate embodiment of the capped catheter assembly of the invention.

FIG. 7 shows an alternate embodiment of the invention. As shown the distal member 70 with finger grip 72 is provided with an externally threaded shoulder 74. Threaded shoulder 74 is adapted to receive internal threads 76 of outer protective cap 78. Outer protective cap 78 preferably contains a sponge 80 saturated with an antiseptic. The outer protective cap 78 is spaced from proximal member or injection cap 82 to permit antiseptic to bathe the exterior surfaces of distal member 70, proximal member 82, and self-sealing septum 84. This maintains the self-sealing septum 84, proximal member 82 and interconnection between proximal member 82 and distal member 70 in aseptic conditions.

The embodiment of FIG. 7 is preferably circular in cross section to facilitate joining of the outer protective cap 78 to distal member 70 through threads 74 and 76.

Also, proximal member or injection cap 82 can be internally threaded to engage exterior threads of female luer member not shown in distal member 70.

Another advantage of the catheter assembly of the invention is the longer length compared with prior art catheter assemblies. Increased length brings a needle only into contact with rigid plastic surfaces which provides increased safety for the flexible catheter tubing 18 during injections.

It can be appreciated from the above description that the catheter assembly described above provides a significant step in the catheter art.

Various modifications are contemplated and can be resorted to by those skilled in the art without departing from the spirit and scope of the invention as defined in the following appended claims.

We claim:

1. A coupler for a catheter assembly comprising:
   a first member having walls and a main tubular member which define a first through passage for fluid communication with a catheter tube at one end of said first through passage, said tubular member having first interconnecting means substantially at the opposite end of said first through passage;
   a second member having walls and a central tubular portion defining a second through passage therein with at least a portion of said central tubular portion being enclosed by an outer skirt, said second member having second interconnecting means disposed within said skirt adapted for separable interconnection with said first interconnecting means of said first member, said main tubular member of said first member and said central tubular portion of said second member proportioned and cooperative to provide a liquid seal when interconnected by insertion of said central tubular portion of said second member into said main tubular member of said first member for communication between said first through passage, said second through passage, and a catheter tube;
   a self-sealing material disposed within the end of said second through passage which is opposite that end forming said liquid seal which self-sealing material forms a barrier to entry of particulates and contaminants to said second through passage but which can be sealingly penetrated by a hollow needle for introduction of liquids;
   a removable outer protective cap for said coupler which covers said second member with said self-sealing material and said interconnection between said first and said second members; and,
   antiseptic means disposed within said protective cap for contacting said second member with said self-sealing material, and said first and second interconnecting means to maintain an aseptic condition.

2. A coupler as claimed in claim 1 wherein:
   said first interconnecting means of said first member has a female luer connection in the form of a proximally extending tubular member having opposed lips, said second interconnecting means of said second member having opposed openings which interlock with said lips for interconnection with said tubular member of said first member by insertion of said second member into said tubular member of said first member, and twisting.

3. A coupler for a catheter assembly according to claim 2 wherein said first member, said second member and said outer protective cap are formed of a plastic material.

4. A catheter assembly comprising in combination the coupler of claim 2 and a catheter tube connected to said first through passage of said first member of said coupler.

5. A coupler according to claim 2 wherein a portion of said second through passage adjacent said end having said self-sealing material has an inward taper to provide an enlarged opening into which said self-sealing member is placed to provide an enlarged exterior surface area of said self-sealing material and an inner tapered guide within said second through passage for receipt of a needle.

6. A coupler assembly comprising a two piece separable coupler comprising a first member having walls defining a through passage, one portion of said passage extending through a bushing for insertion within the lumen of a catheter tube and another portion passing through a female luer connection having a projecting tubular member with a pair of opposed lips disposed on the outer peripheral edge;
   a second member having walls defining a through passage, one portion of which passage terminates in an opening having an end plug of self-sealing material disposed therein, another portion of said passage being formed by a tubular male member, said walls further defining an outer skirt which surrounds said male member and is spaced therefrom to form an inner chamber, said outer skirt having two opposed openings therein, each having a tab, said openings and said tabs being sized and proportioned to engage said opposed lips on said female luer connection upon insertion of said male member within said female luer connection and twisting to form a liquid seal between said first and said second member and communication between said first and said second through passages; and, an outer protective cap extending over and enclosing said second member and having a liquid antiseptic disposed therein for liquid antiseptic contact with at least a portion of said second member, said self-sealing material, said inner chamber, and said interlocking lips and tabs within said first and said second members.

7. A coupler comprising:

a hub assembly having a bushing for insertion within the lumen of a catheter tube and a female connector having at least one tab adapted for interconnection with a male connector, said bushing and said female connector of said hub assembly defining a first through passage therein which communicates with the lumen of a catheter tube by means of said bushing;

an injection cap having a male connector and walls which define a second through passage which communicates with said first through passage of said hub assembly upon interconnection of said male connector with said female connector, said male connector having an outerwall spaced therefrom and substantially coextensive therewith to form an inner chamber, said outer wall having at least one opening therein for interconnection with said at least one tab of said female connector;

self-sealing material placed within the end of said second through passage of said injection cap;

an outer second through passage of said injection cap;

an outer protective cap which covers said self-sealing material and said first and said second interconnecting means; and, an absorptive material containing a liquid antiseptic disposed within said cap for contact of said antiseptic with said self-sealing material, said female connector, said male connector, and said inner chamber.

8. A coupler as claimed in claim 7 wherein:

said injection cap comprises a generally cylindrical flattened housing formed of a clear plastic material and wherein a portion of said second through passage adjacent said end having said self-sealing material has an inward taper to provide an enlarged opening into which said self-sealing member is placed to provide an enlarged exterior surface area of said self-sealing material and an inner tapered guide within said second through passage for receipt of a needle.

9. A coupler for a catheter according to claim 7 wherein:

said hub assembly, said injection cap and said outer protective cap are formed of a plastic material.

10. A coupler as claimed in claim 9 wherein:

said injection cap is formed of a plastic which has a durometer value which is less than the durometer value of the plastic forming said hub assembly.

11. A catheter assembly comprising in combination the coupler of claim 7 and a catheter tube connected to said bushing.

12. A method for preserving in an aseptic condition the exposed open end of a coupler attached to the trailing end of a catheter tube comprising:

interconnecting said exposed open end of said coupler with an exposed open end of a through passage of an injection cap having a self-sealing material disposed within the opposite end of said through passage; and, enclosing said self-sealing material and said interconnecting open ends of said coupler and said injection cap with an outer protective separable cap having an absorbent material containing a liquid antiseptic disposed therein for contact of said liquid antiseptic with said self-sealing material and said interconnecting open ends of said coupler and said injection cap.

* * * * *